United States Patent [19]
Shorr

[11] Patent Number: 5,219,923

[45] Date of Patent: Jun. 15, 1993

[54] ELECTROPHORETIC MEDIA

[75] Inventor: Robert Shorr, Overbrook Hills, Pa.

[73] Assignee: AT Biochem, Inc., Malvern, Pa.

[21] Appl. No.: 568,237

[22] Filed: Aug. 15, 1990

Related U.S. Application Data

[63] Continuation-in-part of Ser. No. 496,338, Mar. 20, 1990, abandoned, which is a continuation-in-part of Ser. No. 331,222, Mar. 21, 1989, Pat. No. 5,055,519, which is a continuation-in-part of Ser. No. 188,467, Apr. 29, 1988, abandoned.

[51] Int. Cl.$^5$ .............................................. C08L 33/00
[52] U.S. Cl. ................................... 524/827; 524/831; 524/833; 524/916
[58] Field of Search ...................... 524/458, 827, 831

[56] References Cited

U.S. PATENT DOCUMENTS

| | | | |
|---|---|---|---|
| 4,189,370 | 2/1980 | Boschetti | 204/299 R |
| 4,243,507 | 1/1981 | Martin et al. | 204/301 |
| 4,388,428 | 6/1983 | Kuzma et al. | 523/106 |
| 4,415,428 | 11/1983 | Nochumson et al. | 204/299 R |
| 4,548,869 | 10/1985 | Ogawa et al. | 428/474.7 |
| 4,548,870 | 10/1985 | Ogawa et al. | 428/474.7 |
| 4,579,783 | 4/1986 | Ogawa et al. | 428/475.2 |
| 4,582,868 | 4/1986 | Ogawa et al. | 524/211 |
| 4,652,354 | 3/1987 | Place et al. | 204/182.8 |
| 4,654,132 | 3/1987 | Takagi et al. | 204/182.8 |
| 4,657,656 | 4/1987 | | 299 R/ |
| 4,660,641 | 7/1986 | Ogawa et al. | 428/355 |
| 4,695,354 | 9/1987 | Sugihara et al. | 204/180.1 |
| 4,699,705 | 10/1987 | Ogawa et al. | 204/299 R |
| 4,806,434 | 2/1989 | Ogawa | 428/474.4 |

FOREIGN PATENT DOCUMENTS

| | | |
|---|---|---|
| 0126639 | 11/1984 | European Pat. Off. |
| 0169397 | 1/1985 | European Pat. Off. |
| 0246873 | 11/1987 | European Pat. Off. |

OTHER PUBLICATIONS

*Electrophoresis* 1988, 9, 157–161.

Primary Examiner—John C. Bleutge
Assistant Examiner—Mark Sweet
Attorney, Agent, or Firm—Woodcock, Washburn, Kurtz, Mackiewicz & Norris

[57] ABSTRACT

Electrophoretic media based on polymers with novel structures are disclosed. The polymers are formed by polymerization of acrylamide monomers, such as N-methylolacrylamide, with cross-linking agents or comonomer agents such as tetraethylene diacrylate and bisacrylamide methylether.

12 Claims, No Drawings

ELECTROPHORETIC MEDIA

RELATED APPLICATIONS

This is a continuation-in-part of U.S. Ser. No. 496,338, filed Mar. 20, 1990 now abandoned, which is in turn a continuation-in-part of U.S. Ser. No. 331,222, filed Mar. 21, 1989, now U.S. Pat. No. 5,055,519 which is in turn a continuation-in-part of U.S. Ser. No. 188,467, filed Apr. 29, 1988, now abandoned. The disclosure of U.S. Ser. No. 331,222 is hereby incorporated by reference.

BACKGROUND OF THE INVENTION

This invention relates to novel electrophoretic media. The media preferably comprise polymer gels which exhibit greater strength, resolution and recoverability of separated products such as DNA than commercially available gels. The media can also be otherwise formulated, such as in bead form and as a surface coating.

During the last decade, considerable advances have been made in molecular biology revolving around the ability to manipulate peptides, DNA and RNA. These advances have fueled the emergence of the biotechnology industry, with extensive research and development geared to the production of biopharmaceuticals, genetically engineered vaccines, immunochemicals, organisms, plants and novel diagnostics. Electrophoresis, a technique in which complex biological substances such as proteins, peptides, DNA and RNA are separated according to size and/or charge, is a powerful separation method widely used within every life science discipline. The procedure is used for the resolution and isolation of complex biological substances such as proteins, peptides, DNA and RNA, and is thus a technique upon which the emerging biotechnology industry is greatly dependent. The needs of the industry have placed new and increased demands on electrophoretic technology, there being a considerable need for electrophoretic media which can provide improved resolution, handleability, and recovery and a range of matrix pore sizes which can be used in newly discovered applications. Most analytical electrophoresis methods are based on zone electrophoresis in which a thin zone of a sample is applied to the electrophoretic medium. When the components of the sample are to be separated according to their charge, an electric potential is applied to the electrophoretic medium for a certain period of time, so that charged components of the sample move in various distances depending on their chemical natures. When the components of the sample are to be separated according to their size, the electrophoretic medium contains a denaturing agent so that components of the sample move in various distances depending on their molecular weights. The migration of the sample components results in the formation of fractional zones which can then be examined and studied by application of standard electrophoretic practices such as fixing, staining, and washing to remove buffers. Typically, the electrophoretic medium is a thin gel slab supported by a suitable material, commonly glass or plastic.

Various hydrophilic colloids, such as starch, cellulose acetate and agarose have been used in the forming of electrophoretic gel slabs, but polyacrylamide is generally favored. Polyacrylamide is used as a cast material composed of varying amounts of acrylamide and bis-acrylamide. $N,N^1$-bis-acrylylcystamine, $N,N^1$-dihydroxy ethylene bis-acrylamide, and $N,N^1$-diallyltartardiamide have also been used. These materials are conventionally proportioned to prepare, on polymerization, a network of polymeric fibers for sieving or anti-convection. Viscosity of the gel is adjusted by varying the amounts of acrylamide and bis-acrylamide. Frequently used catalyst and initiator are TEMED (tetraethylaminediamine) and ammonium persulfate or riboflavin/light.

Methods known in the art for utilizing polyacrylamide gels for determination of nucleotide sequences involve the preparation of the gels in given thicknesses, such as between glass plates to a thickness of approximately 0.3 mm. In some applications the gel may be polymerized onto a support film. DNA samples labeled such as with $^{32}P$, $^{35}S$ or fluorescent dyes are placed onto sample slots and electrophoresed. After electrophoresis (1–24 hours) the gel is removed from the glass plates and autoradiography performed. In automated systems, fluorescent labeled nucleotides are monitored during the separation. Autoradiography requires 10 to 20 hours after which time films are studied to determine nucleotide sequence. The preparation of gels for autoradiography of $^{35}S$ nucleotides requires immersion in 10% acetic acid to remove urea and handling of the gels with caution due to extreme fragility.

When proteins are being separated by electrophoretic methods based on their size, sodium dodecyl sulfate (SDS) is generally added to the polyacrylamide gel alone, or in conjunction with other denaturants, to unfold the protein and provide a net negative charge. Molecular sizes can be estimated from mobilities as compared to known standards. When separations are being made according to charge, the polyacrylamide gels are generally used in combination with acidic, basic or neutral buffer systems in the absence of denaturing agents. Electrodes are positioned according to the predicted net charge of the sample at the pH used.

Despite the widespread use of polyacrylamide gels to separate complex proteins, double or single stranded DNA, synthetic oligonucleotides and the like as well as for DNA sequencing, a number of disadvantages are associated with polyacrylamide. Among them are neurotoxicity, short shelf life, cumbersome preparation, and gel fragility. Neurotoxicity and instability have only recently been addressed in the development of adequate precast polyacrylamide gels. Gel fragility is considered a major difficulty in DNA sequencing where ultrathin gels are required for optimum resolution on autoradiography of radiolabeled nucleotides. These disadvantages are also found in other applications of electrophoresis such as separation of proteins.

Recognizing the shortcomings of polyacrylamide gels, many have attempted to improve the gels. U.S. Pat. No. 4,657,656 to Ogawa discloses an improved medium for electrophoresis comprising a polyacrylamide gel formed by crosslinking polymerization of an acrylamide compound and a crosslinking agent and further containing a water soluble polymer having a molecular weight in the range of 10,000 to 1,000,000, such as polyvinyl alcohol or polyacrylamide. Incorporation of the water soluble polymer such as solid polyacrylamide is said to reduce the brittleness of the polyacrylamide gel. Crosslinking agents disclosed as being suitable are N,N'-methylenebisacrylamide, N,N'-propylenebisacrylamide, diacrylamide dimethylether, 1,2-diacrylamide ethyleneglycol, ethyleneureabisacrylamide, ethylene diacrylate, N,N'-diallyltartardiamide and N,N'-bisacrylylcystamine.

U.S. Pat. No. 4,695,354 to Sugihara et al. discloses that conventional thin polyacrylamide gels are unsuitable because, when used to resolve nucleic acid fragments, they give distorted patterns. Sugihara et al. disclose that the resolution of the gels can be improved by incorporating into the gels less than 1 wt/v% of glycerol.

The fragility and brittleness of conventional polyacrylamide gel membranes can lead to problems when it is desired to dry the membranes for enhanced resolution. As disclosed in U.S. Pat. No. 4,699,705 to Ogawa et al., in the drying process, the adhesion between the glass plate and the membrane is negligible, the membrane is easily broken. To alleviate these problems, Ogawa et al. disclose that the adhesion between the membrane and its support can be enhanced by utilizing as the support a polymer sheet which has been subjected to glow discharge treatment. The patent also suggests the incorporation in the gel medium of at least one carbamoyl group-containing compound, such as urea or formamide, as modifier. Other methods disclosed for improving the adhesion between a polyacrylamide gel membrane and its support involve the use of special adhesives as disclosed in U.S. Pat. Nos. 4,548,869, 4,548,870, 4,579,783 and U.S. Pat. No. 4,600,641 to Ogawa et al. and in U.S. Pat. No. 4,415,428 to Nochumson et al.

U.S. Pat. No. 4,582,868 to Ogawa et al. notes that the polymerization reaction for the preparation of polyacrylamide can be inhibited by the presence of oxygen. It discloses a novel medium for electrophoresis in the form of an aqueous gel which can be prepared in the presence of oxygen. The novel medium is an acrylamide copolymer having a specifically selected repeating unit.

U.S Pat. No. 4,189,370 to Boschetti discloses gel polymers prepared by radical polymerization of N-methylol-acrylamide and a bifunctional allylic or acrylic compound causing cross-linking to yield a tridimensional configuration polymer. Examples of cross-linking agents disclosed in the patent are N,N'-methylene bisacrylamide, diallyltartramide and ethylenediacrylate.

Despite the great amount of effort which has gone into improving conventional polyacrylamide gels, there is still a need for new gels which overcome the problems associated with acrylamide gels such as brittleness, neurotoxicity, cumbersome preparation and short shelf life. There is also a need for new gels which have greater resolution power and recoverability of separated DNA and protein materials to meet the demands of the emerging biotechnology industry.

SUMMARY OF THE INVENTION

Electrophoretic media based on polymers with novel structures have now been found which provide improved resolution and overcome many of the disadvantages associated with conventional polyacrylamide and agarose gels. More particularly, this invention relates to an electrophoretic medium consisting essentially of an aqueous gel formed by crosslinking polymerization in the presence of aqueous medium and in the absence of oxygen of one or more acrylamide compounds in the presence of one or more crosslinking or comonomer agents selected from the group consisting of ethyoxylated trimethylpropane triacrylate, diethyleneglycol diacrylate, diacetone acrylamide, pentaerythritolacrylate, polyalkoxylated aliphatic triacrylate, 1,3-butyleneglycol diacrylate, tetraethylene glycol diacrylate, bisacrylamide methylether and tris-(2-hydroxyethyl)isocyanurate triacrylate.

By virtue of the different combinations of monomers and cross-linkers, the resulting gels have polymer structures chemically and architecturally different from those of conventional polyacrylamide gels, and tests indicate that they offer the advantages of greatly improved resolution, greater strength and thermal characteristics over the conventional gels.

In addition to the aforementioned electrophoretic media, this invention relates to the polymerization mixtures from which such media are prepared, i.e., the mixture of components such as monomers, cross-linking agents and catalysts, detergents and buffers which are used to prepare the electrophoretic media. This invention also relates to the novel polymers prepared by the cross-linking polymerization of the above-mentioned monomers and cross-linking agents. This invention also relates to beads formed by cross-linking polymerization of the above-mentioned monomers and cross-linking agents. Finally, this invention also relates to electrophoretic methods for effecting chromatographic separation of components in a chemical mixture using the above-mentioned electrophoretic media.

DETAILED DESCRIPTION OF THE INVENTION

As indicated above, the novel gels and electrophoretic media of this invention have polymer structures significantly different from the structures of conventional polyacrylamide and agarose gels.

The acrylamide compounds which may be used to prepare the materials of this invention include acrylamide and related acrylamide compounds such as N,N-dimethylacrylamide, N-methylolacrylamide, and N-methylacrylamide.

To prepare the polymer gels of this invention, the monomer(s) and cross-linking agent(s) are dissolved or dispersed in aqueous medium (water or a mixture of water with other organic solvents such as dimethylformamide) to prepare an aqueous solution or dispersion in which the crosslinking polymerization reaction is carried out. It is important that the polymerization reaction be carried out in the absence of oxygen. The relative amounts of monomer and cross-linking agent used will vary with the application for which the gel is to be used. Generally, however, the crosslinking agent can be employed in an amount of approximately 1 to 30 wt. %, preferably 2 to 10 wt. %, based on the total weight of the monomer and the crosslinking agent. The preferable gel concentration is such that the amount of monomer and cross-linking agent in the gel is 1.5% to 15% by weight.

A particularly preferred cross-linking agent is the compound bisacrylamide methylether (BAME), used either alone as cross-linking agent or in combination with other cross-linkers.

The crosslinking polymerization reaction by which the novel gels of this invention are prepared is generally carried out in an aqueous medium and can be initiated by known initiators or polymerization catalysts. Suitable free radical-providing catalyst systems are benzoyl peroxide, t-butylhydroperoxide, lauroyl peroxide, cumene hydroperoxide, tetralin peroxide, acetyl peroxide, caproyl peroxide, t-butylperbenzoate, t-butyldiperphthalate, methylethylketone peroxide, hydrogen peroxide-Fe2+-ascorbic acid, riboflavin-light, and various persulfate salts in conjunction with N,N,N',N'- tetramethylethylenediamine (TEMED), diethylmethylaminediamine (DEMED), B-dimethylaminopropionitrile or similar reagents and ammonium persulfate-metabisulfite. Another class of free radical generating catalysts are azocatalysts such as azodiiosobutyronitrile, azodiisobutryamide, azobis (dimethylvaleronitrile) azobis(methylbutyronitrile, dimethyl, diethyl, or dibutylazobismethylvalerate. These and similar reagents contain a N,N double bond attached to aliphatic carbon atoms, at least one of which is tertiary. The amount and type of catalyst and initiator is generally indicated by the nature and concentrations of the monomer and crosslinkers used. The optimum amount of catalyst is also affected by the presence of any accompanying impurities. Generally speaking, however, the catalyst can be employed in the amount of approximately 0.3 to 5 wt. % based on the total amount of the monomer and crosslinking agent. The preferred initiator and catalyst system is TEMED or DEMED and a persulfate salt.

Various buffer systems, denaturing agents or other modifiers (as required by the technique), may be included in the polymerization mixture. Examples of buffer systems suitable for use in the invention are:

| COMMON BUFFER SYSTEMS USED IN ELECTROPHORESIS | |
|---|---|
| Buffer | pH |
| Citrate-phosphate | 3.2 |
| Succinate | 5.2 |
| Phosphate-magnesium sulfate | 6.8 |
| Tris-EDTA-acetate | 7.2 |
| Tris-HCl-magnesium sulfate | 7.4 |
| Tris-EDTA-acetate | 7.8 |
| Tris-magnesium chloride | 8.0 |
| Tris-EDTA-borate | 8.3 |
| Tris-EDTA-borate | 8.6 |
| Tris-EDTA-lactate | 8.6 |
| Tris-veronal | 8.6 |
| Veronal | 9.2 |
| Tris-EDTA-borate | 9.5 |
| Tris-EDTA-phosphate | 8.6 |
| Tris-glycine | 8.8 |
| Tris-glycine-SDS | 8.8 |
| Sodium phosphate | 7.5 |
| Sodium-phosphate SDS | 7.5 |
| Ethanolamine/GABA* | 9.5-10 |
| Tris-acetate/GABA | 9.6-10.2 |
| Ammediol/GABA | 9.6-10.2 |
| Ammediol/HCl | 9.6-10.2 |
| Tris-HCl | 9.3-9.6 |

*GABA = gamma, amino butyric acid

Tests have indicated that the preferred buffer may vary both with the particular polymer matrix utilized and the desired application. For example, the gels described below as "Gels I and II" are particularly useful for electrophoresis of DNA. Of the two, Gel II, containing a small amount of BAME, is highly preferable. The buffer system Tris-borate-EDTA has utilized with this gel with great success; excellent results have also been obtained using Tris-glycine buffer systems. The gels described below as "Gels III and IV" are particularly useful for electrophoresis of proteins, with Gel IV, containing a small amount of BAME, being the preferred gel among the two. The buffer Tris-glycine-SDS has been used with the protein gels with excellent results. Finally, the gels described below as "Gels V and VI" are particularly useful for sequencing of DNA, with Gel VI being the preferred gel among the two.

Best results have been achieved with the sequencing gels using the following buffer systems: Tris-borate-EDTA and Tris-glycine.

It is often preferred to incorporate in the gel a urea modifier to maintain the samples in a denatured state. The modifier can be used in an amount of approximately 40 to 60 wt. % based on the volume of the aqueous gel containing the monomer and crosslinking agent.

Other specific examples of denaturing agents which may be incorporated into the electrophoretic media of the invention include N,N-dimethylformamide; n-propyl alcohol; formamide; dimethylformamide; and glycine.

As previously indicated, gels within the scope of this invention may be used for various applications as diverse as separation of proteins, DNA and DNA sequencing. The end uses of the gels will depend heavily on the monomer and cross-linking agent composition as well as on the nature of the additives such as buffers, detergents and catalysts contained in the overall electrophoretic medium. Table I lists monomer/comonomer, crosslinker combinations which have been utilized to prepare gels according to this invention and also indicates the types of electrophoretic applications which have been found to be suitable for each type gel.

TABLE I

| Monomer* | Comonomer, Cross-linker* | Applications** |
|---|---|---|
| n-methylol-acrylamide | Ethoxylated trimethylpropane triacrylate (EDTA) | P, DNA |
| n-methylol-acrylamide | Diethyleneglycol diacrylate | P, DNA |
| n-methylol-acrylamide | Diacetone acrylamide (DAA) | DNA |
| n-methylol-acrylamide | Pentaerythritolacrylate | P, DNA |
| n-methylol-acrylamide | Polyalkoxylated aliphatic triacrylate (sold by Sartomer Company, West Chester, PA) | P, DNA |
| n-methylol-acrylamide | 1,3 Butyleneglycol diacrylate (BGDA) | P, DNA |
| n-methylol-acrylamide | Tetraethylene glycol diacrylate (TEGDA) | P, DNA |
| n-methylol-acrylamide | Tris (2-hydroxyethyl)isocyanurate triacrylate (THICTA) | S |
| n-methylol-acrylamide | Bisacrylamide methyl ether (BAME) | P, DNA, S |

*Generally, the amount of monomer in these aqueous gels ranged from 2.5 to 15%, and the amount of comonomer ranged from 0.025 to 0.5%.
**P = useful for protein separations, DNA = useful for separation of DNA; S = useful for DNA sequencing.

A gel medium according to this invention which is suited to one use may not, and probably will not be, suited for another use. Examples of specifically preferred gel compositions according to this invention are presented blow. As previously mentioned, Gels I and II have been found to be particularly useful for electrophoresis of DNA strands, Gels III and IV have been found to be particularly useful for the electrophoresis of proteins, and Gels V and VI have been found to be particularly useful for DNA sequencing.

| Major Components: | |
|---|---|
| Gel I | |
| N-methylolacrylamide (NMA) (48% w/v) | 5.26 ml |
| Tetraethyleneglycoldiacrylate (TEGDA) | 0.016 ml |
| 10 × Tris-borate-EDTA | 5 ml |
| TEMED | 0.1 ml |
| Water to | 48.8 ml |
| 10% w/v Ammonium persulfate (APS) | 0.2 ml |

-continued

| Major Components: | |
| --- | --- |
| Gel II | |
| N-methylolacrylamide (NMA) (48% w/v) | 5.26 ml |
| Bisacrylamidemethylether (BAME) | 0.28 g |
| Tetraethyleneglycoldiacrylate (TEGDA) | 0.016 ml |
| 10 × Tris-borate - EDTA | 5 ml |
| TEMED | 0.1 ml |
| Water to | 48.8 ml |
| 10% w/v Ammonium persulfate (APS) | 0.2 ml |
| Gel III | |
| NMA | 5.26 ml |
| TEGDA | 0.025 ml |
| 0.75M Tris-HCl pH 8.8 | 25 ml |
| 10% Sodium Dodecylsulfate (SDS) | 0.5 ml |
| TEMED | 0.1 ml |
| Water to | 48.5 ml |
| 10% APS | 0.5 ml |
| Gel IV | |
| NMA | 5.26 ml |
| BAME | 0.28 g |
| 0.75M Tris-HCl pH 8.8 | 25 ml |
| 10% Sodium Dodecylsulfate (SDS) | 0.5 ml |
| TEMED | 0.1 ml |
| Water to | 48.5 ml |
| 10% APS | 0.5 ml |
| Gel V | |
| DAA | 0.67 g |
| Acrylamide | 2.7 g |
| BGDA | 0.021 ml |
| THICTA | 0.048 g |
| TEMED | 0 05 ml |
| 10 × TBE | 5 ml |
| Water to | 48.6 ml |
| 10% APS | 0.4 ml |
| Gel VI | |
| Acrylamide | 4 g |
| NMA | 2.1 ml |
| BAME | 0.15 g |
| 1 × Tris-Borate EDTA | 10 ml |
| Urea | 48 g |
| 10% APS | 800 μl |
| TEMED | 80 μl |
| water to | 100 ml |

Membranes made from the aqueous gel media of this invention generally have a thickness in the range of approximately 0.1 mm to approximately 3 mm, preferably in the range of approximately 0.2 to 1.5 mm. The gel membranes of this invention can also, however, be made very thin, e.g., to a thickness of less than 0.1 mm, and yet exhibit excellent resiliency and resolution.

The aqueous gel media of this invention can be used for electrophoretic applications by methods well known in the art. By way of example, the following is a description of how the "DNA" gel described above as Gel II might be used:

Gel II is useful for separating double-stranded or single-stranded fragments of DNA linearly in the range from 10 to 600 bases. The gels may be polymerized between glass plates of standard vertical electrophoresis apparatus. A 10% gel is useful for separating fragments in the size range 5 to 150 base pairs; a 5% gel is useful for separating from 100 to 600 base pairs. Denaturing for synthetic oligonucleotide purifications can be accomplished using normal denaturing conditions (such as urea).

In more detail, Gel II may be prepared as follows. This procedure describes the preparation of 50 mls of the gel, a sufficient amount for a 14×14 cm gel with a 1.5 mm spacer.

10% Gel (5 to 150 base pairs)

1. Wash and assemble glass plates according to manufacturer's instructions.
2. Place 25 mls. of gel solution into a clean beaker.
3. Add 5 mls of 10×TBE buffer concentrate.
4. Add 19.7 mls of deionized water.
5. Add 100 μl of TEMED.
6. Add 200 μl of fresh 10% ammonium persulfate.
7. Swirl the solution gently and immediately pour the gel solution to the top of the glass plates by utilizing a syringe without a needle or a 25 ml pipette.
8. Insert the sample comb and llow 15-30 minutes for complete polymerization.

5% Gel (100 to 600 base pairs)

1. Prepare plates as described above in step 1 of 10% gel.
2. Place 12.5 mls of gel solution into a clean beaker.
3. Add 5 mls of 10×TBE buffer concentrate.
4. Add 32.2 mls of deionized water.
5. Add 100 μl of TEMED.
6 Add 200 μl of fresh 10% ammonium persulfate.
7. Follow steps 7 and 8 from 10% gel.

Electrophoresis

1. Prepare sufficient 1×TBE buffer for upper and lower buffer chambers.
2. Assemble electrophoresis apparatus according to manufacturers' directions.
3. Carefully remove the sample well comb and wash the wells with 1×TBE buffer.
4. Add approximately 1 μg of sample in 4-10 μl to each well. Load more DNA if interested in very small bands.
5. The gels are run at 200V constant voltage for approximately 1½ hours or until Orange G tracking dye has reached the bottom of the plate.
6. Remove the glass plates and stain the gels with ethidium bromide (1-5 μg/ml).

Sample Preparation

Gel II has been found to be superior to standard polyacrylamide gels particularly in resolution of small DNA fragments. Thus, a single gel can accomplish that which if possible would require multiple runs on different concentration polyacrylamide gels. Tests indicate that other gels within the scope of this invention are also highly suited for electrophoretic applications and are superior to standard polyacrylamide and agarose gels for the same reasons. Gel IV also provides substantial improvement in resolution over standard polyacrylamide gels for proteins particularly in the protein size range 20-205 kd. Gel V shows markedly improved ease of handling, and demonstrates an increase of 10% in the number of bases which can be read over a 4% polyacrylamide gel. In comparison to a 6% polyacrylamide gel (more similar in handling characteristics) a 75% increase in bases read is observed.

The materials described herein for use as gels can also be prepared as porous, non-porous, or macroreticular beads of any dimension for use in electrophoretic applications. In preparing beads several polymerization conditions well known in the art can be used. A preferred method is suspension polymerization in a liquid which is not a solvent for the materials used. This method produces the polymer in the form of spheroid beads the size of which can be regulated and controlled by the composition of the suspending medium and the rate of agitation during polymerization. The determination of the most effective conditions vary from case to case, depending on the materials chosen, their amounts and relative proportions. Polymerization may also be carried out in the presence of a precipitant, i.e., a liquid which acts as a solvent for the mixture and is chemically inert under the polymerization conditions. The solvent must be present in such amounts as to exert little solvating action. On polymerization phase separation of the product takes place. The exact solvents used are determined and optimized empirically for each mixture. A typically used inverse suspension polymerization involves a small amount of water in a hexane solution stirred very fast with initiators present. The polymerizing materials will stay in the water droplets depending on their hydrophilic properties.

Beads prepared from the above described materials may also be useful for the separation of DNA, RNA, proteins and peptides in a chromatography format. Separation can be adjusted to occur via interaction or be based on size. Interactive chromatography can result from ion-exchange, hydrophobic, or other modes directly with the bead materials or with modifiers or substituted chemical groups added pre- or post-polymerization.

The materials described can also be used for the preparation of gels or beads, alone or in conjunction with other materials or attached to any surface, for the purpose of providing nutrients and support for bacterial or cellular growth for any purpose. Examples are polymerizing in and/or placing gels or beads alone or in conjunction with other materials in petri dishes or by coating (covalently or non-covalently) glass, metal, plastic, teflon, paper of any composition, polyvinylchloride, silica or other surfaces. Applications may include bacterial smears for diagnostic purposes or provisions of attachment sites for cell growth. A further example of such a material is polyvinylchloride papers impregnated with silica or glass. Coating of these surfaces with a function capable of participating in the polymerization process would allow direct polymerization and covalent attachment of the material to the support.

In addition to these applications it is also feasible to include into the polymerization mixture proteins, peptides, pharmaceuticals, silica, or electron conductive materials. The above materials could be used for a variety of applications including drug delivery, artificial organs or parts thereof and plastic type conductors of electricity.

What is claimed is:

1. An electrophoretic medium consisting essentially of an aqueous gel formed by polymerization in the presence of aqueous medium and in the absence of oxygen of one or more acrylamide monomers in the presence of one or more different crosslinking or comonomer agents selected from the group consisting of diethyleneglycol diacrylate, diacetone acrylamide, pentaerythritolacrylate, 1,3-butyleneglycol diacrylate, tetraethylene glycol diacrylate, bisacrylamide methylether and tris-(2-hydroxyethyl)isocyanurate triacrylate.

2. An electrophoretic medium of claim 1 wherein said acrylamide monomer is N-methylolacrylamide.

3. An electrophoretic medium of claim 1 wherein said crosslinking agent or comonomer comprises diethyleneglycol diacrylate.

4. An electrophoretic medium of claim 1 wherein said crosslinking agent or comonomer comprises diacetone acrylamide.

5. An electrophoretic medium of claim 1 wherein said crosslinking agent or comonomer comprises pentaerythritolacrylate.

6. An electrophoretic medium of claim 1 wherein said crosslinking agent or comonomer comprises 1,3-butyleneglycol diacrylate.

7. An electrophoretic medium of claim 1 wherein said crosslinking agent or comonomer comprises tetraethylene glycol diacrylate.

8. An electrophoretic medium of claim 1 wherein said crosslinking agent or comonomer comprises tris-(2-hydroxyethyl)isocyanurate triacrylate.

9. An electrophoretic medium of claim 1 wherein said crosslinking agent or comonomer comprises bisacrylamide methylether.

10. An electrophoretic medium of claim 7 wherein said acrylamide monomer is N-methylolacrylamide.

11. An electrophoretic medium of claim 9 wherein said acrylamide monomer is N-methylolacrylamide..

12. A polymerization mixture for preparing the electrophoretic medium of claim 1 comprising one or more acrylamide monomers and one or more crosslinking agents selected from the group consisting of diethyleneglycol diacrylate, diacetone acrylamide, pentaerythritolacrylate, 1,3-butyleneglycol diacrylate, tetraethylene glycol diacrylate and tris-(2-hydroxyethyl)isocyanurate triacrylate; a polymerization catalyst; and aqueous medium.

* * * * *